(12) United States Patent
Takayama et al.

(10) Patent No.: US 7,632,463 B2
(45) Date of Patent: Dec. 15, 2009

(54) ANALYSIS APPARATUS AND CONDENSER

(75) Inventors: Hidehito Takayama, Yokohama (JP);
Haruyo Saitou, Yokohama (JP)

(73) Assignee: Mitsubishi Kagaku Iatron, Inc., Tokyo (JP)

( * ) Notice: Subject to any disclaimer, the term of this patent is extended or adjusted under 35 U.S.C. 154(b) by 770 days.

(21) Appl. No.: 11/274,923

(22) Filed: Nov. 15, 2005

(65) Prior Publication Data
US 2006/0182660 A1   Aug. 17, 2006

(51) Int. Cl.
*G01N 21/00* (2006.01)
(52) U.S. Cl. .................................. 422/82.05
(58) Field of Classification Search .............. 422/82.05
See application file for complete search history.

(56) References Cited

U.S. PATENT DOCUMENTS 6,304,527 B1 * 10/2001 Ito et al. ................... 369/44.23

FOREIGN PATENT DOCUMENTS

| EP | 0 062 160 | 10/1982 |
|---|---|---|
| JP | 57-171245 | 10/1982 |
| JP | 58-214842 | 12/1983 |
| JP | 62-201047 | 12/1987 |
| JP | 5-261110 | 10/1993 |
| JP | 9-184808 | 7/1997 |
| JP | 11-23529 | 1/1999 |
| JP | 11-094747 | 4/1999 |
| JP | 2001-238674 | 9/2001 |
| JP | 2001-337083 | 12/2001 |
| JP | 2002-221486 | 8/2002 |
| JP | 2003-4629 | 1/2003 |
| JP | 2003-294629 | 10/2003 |

OTHER PUBLICATIONS

Lee, H. J.; Goodrich, T.T.; Corn, R. M. SPR Imaging Measurements of 1-D and 2-D DNA Microarrays created from Microfluidic Channels on Gold Thin Films. Analytical Chemistry, 2001, 73, 22, pp. 5525-5531.*
P1S18A 1×8 Optical Switch, pamphlet, Omron Corporation, Jul. 2003.
PS141A 4+1 Optical Switch, pamphlet, Omron Corporation, Jul. 2003.
P1AA Valuable Optical Attenuator, pamphlet, Omron Corporation, Jul. 2003.

* cited by examiner

*Primary Examiner*—Walter D Griffin
*Assistant Examiner*—Bobby Ramdhanie
(74) *Attorney, Agent, or Firm*—Katten Muchin Rosenman LLP

(57) ABSTRACT

The object of the present invention is to provide an analysis apparatus that makes it possible to detect lights from a plurality of spots formed on an analysis chip without the lack of positioning accuracy while detecting the lights and the instability of holding the samples in spite of the downsized construction thereof.

To achieve such an object as mentioned above, the analysis apparatus of the present invention for analyzing samples by means of detecting lights from a plurality of spots formed on an analysis chip so as to hold the samples comprising: a chip holder for holding the analysis chip; a light-sensitive detector for detecting lights from the spots; and a selectively light-transmitting unit for transmitting lights selectively from the desired spots to the light-sensitive detector, in a state where the analysis chip is held by the chip holder.

30 Claims, 9 Drawing Sheets

ANALYSIS APPARATUS AND CONDENSER

BACKGROUND OF THE INVENTION

1) Field of the Invention

The present invention relates to an analysis apparatus for analyzing samples in areas such as chemical analysis or biological analysis, and specifically, to an analysis apparatus for conducting the optical analysis by means of detecting lights from spots formed on an analysis chip and holding the samples thereon, and also relates to a condenser used in the analysis apparatus.

2) Description of the Related Art

Currently, in areas such as the chemical analysis or the biological analysis, optical analyses including the fluorescence analysis, surface plasmon resonance analysis, chemiluminescence analysis, bioluminescence analysis, electrochemiluminescence analysis, and radioisotope analysis are conducted for analyzing various samples.

In these analyses, lights generated from spots on an analysis chip, or reflection lights and transmitted lights from the spots irradiated are detected, generally in a state where the samples are held on the spots. A plurality of spots are generally formed on the analysis chip so as to conduct the analysis efficiently. An analysis apparatus is used for the purpose of detecting the lights.

FIG. 16 shows schematically a substantial part of a conventional optical analysis apparatus used for analyzing samples by means of detecting fluorescence. As illustrated in FIG. 16, the analysis apparatus has an analysis chip 101 formed a plurality of spots 102 thereon. Each spot 102 holds a sample such as protein labeled by a fluorescent material. The analysis apparatus further has a light source 103 for irradiating an excitation light upon the analysis chip 101 and a light-sensitive detector 104 for detecting the light from the analysis chip 101.

On conducting the analysis using this conventional analysis apparatus, the excitation light from the light source 103 is irradiated onto the analysis chip 101 first. Then the sample on the spot 102 is excited by the excitation light irradiated and fluorescence is emitted from the spot 102. Then the analysis is conducted with the light-sensitive detector 104 by detecting the fluorescence emitted.

This conventional analysis apparatus detects the light by means of scanning the spots one by one. Thus, the apparatus generally comprises a mechanism for driving to move the light-sensitive detector 104 or the analysis chip 101 so as to move and adjust the position of either the light-sensitive detector 104 or the analysis chip 101. Refer to Japanese Patent Number 3346727 (hereinafter, whenever it is necessary, called simply a patent publication 1) and others.

However, the conventional analysis apparatus such as the patent publication 1 has the following problems. One is that the lack of positioning accuracy while detecting the lights and the instability of holding the samples induced by the moving and the position adjusting of either the light-sensitive detector 104 or the analysis chip 101 deteriorate the light-detecting efficiency and analysis accuracy. Another is the upsizing of the analysis apparatus induced by the necessity for equipping the mechanism of driving the light-sensitive detector 104 and the analysis chip 101.

SUMMARY OF THE INVENTION

The present invention has been made in view of such problems as mentioned above. The object of the invention is to provide an analysis apparatus that has downsized construction and makes it possible to detect lights from a plurality of spots formed on an analysis chip without the lack of positioning accuracy while detecting lights and the instability of holding the samples and to provide a condenser used widely for constructing the analysis apparatus of the present invention.

To achieve such an object as mentioned above, an analysis apparatus of the present invention is the apparatus for analyzing samples by means of detecting lights from a plurality of spots formed on an analysis chip so as to hold the samples comprising: a chip holder for holding the analysis chip; a light-sensitive detector for detecting lights from the spots; and a selectively light-transmitting unit for transmitting lights selectively from the desired spots to the light-sensitive detector, in a state where the analysis chip is held by the chip holder.

And a condenser of the present invention is the condenser used in an analysis apparatus that has a chip holder for holding an analysis chip having a plurality of spots for holding the samples thereon and a light-sensitive detector for detecting lights from the spots, wherein the condenser transmits lights selectively from the desired spots to the light-sensitive detector.

With these constructions, position adjusting of the analysis chip and the light-sensitive detector is not any more required, thereby the positioning accuracy being improved and the stability of holding the samples being realized easily, which lead to the enhanced analysis accuracy. Furthermore, the mechanism for driving the analysis chip and the light-sensitive detector is not any more required, thereby it becomes possible to downsize the analysis apparatus.

As one preferred feature, said selectively light-transmitting unit and said condenser include a light path forming section for forming light paths, each starting from each of the spots to the light-sensitive detector, and a light path selecting unit for transmitting lights selectively from the desired spots to the light-sensitive detector by means of selecting the light paths. With this construction, it is possible to detect the lights from the desired spots only by means of selecting the light paths, which leads to the downsizing of the analysis apparatus with its simple construction.

As another preferred feature, each of said light paths includes a optical transmission medium provided in correspondence with each of the spots and having a light-inputting end for receiving the light from each of the spots and a light-outputting end for outputting the light to the light-sensitive detector. With this construction, the light-sensitive detector can detect the lights from the spots formed on the analysis chip surely.

As still another preferred feature, said selectively light-transmitting unit and said condenser include a light-outputting end holder for holding the light-outputting ends of the optical transmission media on the circumference of the same circle. With this construction, it is possible to select the light paths quickly and thus shorten time to detect the lights from the desired spots. Also the drive system can be simply the rotation drive system, which leads to realizing an inexpensive and downsized analysis apparatus.

As a further preferred feature, said light path selecting unit includes a light-outputting end moving unit for moving the light-outputting ends of the optical transmission media corresponding with the desired spots selectively into positions where optical paths formed by the lights from the desired spots to the light-sensitive detector are established. With this construction, it is possible to simplify the constitution of the analysis apparatus and thus to detect the lights from the desired spots easily.

It is also preferred that said light path selecting unit includes a selectively optical transmission medium having a selected-light inputting end for inputting the lights from the light outputting ends of the optical transmission media and a selected-light outputting end for outputting the light from the selected-light inputting end, and a selected-light inputting end moving unit for moving the selected-light inputting end selectively into a position where optical paths formed by the lights from the desired spots to the light-sensitive detector are established. With this construction, it is possible to simplify the constitution of the analysis apparatus and thus to detect the lights from the desired spots easily. It is also possible to enhance replaceability of light path selecting unit by means of modularizing the unit. Furthermore, the simple constitution makes it possible to reduce the parts count, and the selecting section, which needs to be a delicate structure, can be surrounded by a somewhat strong construction. These characteristics lead to the advantage of the increase in longevity, the prevention of the malfunction, and the improvement in maintenance-bearing capacity.

It is also preferred that said light path selecting unit includes a Garvano mirror arranged to be rotatable for selecting the light paths by reflection so as to establish optical paths formed by the lights from the desired spots to the light-sensitive detector. With this construction, it is possible to select the light paths quickly and to simplify the constitution of the analysis apparatus. It is also possible to enhance replaceability of light path selecting unit by means of modularizing the unit. Furthermore, the simple constitution makes it possible to reduce the parts count, and the selecting section, which needs to be a delicate structure, can be surrounded by a somewhat strong construction, which lead to increase in longevity, prevention of the malfunction, and improvement in maintenance-bearing capacity.

It is also preferred that said light path selecting unit includes a polygon mirror having a plurality of specular surfaces and arranged to be rotatable for selecting the light paths by reflection so as to establish optical paths formed by the lights from the desired spots to the light-sensitive detector. With this construction, it is possible to select the light paths quickly and to simplify the constitution of the analysis apparatus. It is also possible to enhance replaceability of light path selecting unit by means of modularizing the unit. Furthermore, the simple constitution makes it possible to reduce the parts count, and the selecting section, which needs to be a delicate structure, can be surrounded by a somewhat strong construction, which lead to increase in longevity, prevention of the malfunction, and improvement in maintenance-bearing capacity.

It is also preferred that said light path selecting unit includes a prism arranged to be movable for selecting the light paths so as to establish optical paths formed by the lights from the desired spots to the light-sensitive detector. With this construction, it is possible to select the light paths quickly and to simplify the constitution of the analysis apparatus. It is also possible to enhance replaceability of light path selecting unit by means of modularizing the unit. Furthermore, the simple constitution makes it possible to reduce the parts count, and the selecting section, which needs to be a delicate structure, can be surrounded by a somewhat strong construction, which lead to increase in longevity, prevention of the malfunction, and improvement in maintenance-bearing capacity.

It is also preferred that said light path selecting unit includes a light shield arranged to be movable for selecting the light paths by blocking off lights from other spots so as to establish optical paths formed by the lights from the desired spots to the light-sensitive detector. With this construction, it is possible to select the light paths quickly and to simplify the constitution of the analysis apparatus. It is also possible to enhance replaceability of light path selecting unit by means of modularizing the unit. Furthermore, the simple constitution makes it possible to reduce the parts count, and the selecting section, which needs to be a delicate structure, can be surrounded by a somewhat strong construction, which lead to increase in longevity, prevention of the malfunction, and improvement in maintenance-bearing capacity.

It is also preferred that said light path selecting unit includes a light path selecting electrical unit that has a liquid crystal and electrodes and that selects the light paths by applying a voltage to the liquid crystal using the electrodes so as to establish optical paths formed by the lights from the desired spots to the light-sensitive detector. With this construction, it is possible to select the light paths quickly and to simplify the constitution of the analysis apparatus. It is also possible to enhance replaceability of light path selecting unit by means of modularizing the unit. Furthermore, the simple constitution makes it possible to reduce the parts count, and the selecting section, which needs to be a delicate structure, can be surrounded by a somewhat strong construction, which lead to increase in longevity, prevention of the malfunction, and improvement in maintenance-bearing capacity.

It is also preferred that each of said light paths includes a focusing lens for receiving and focusing the lights from each of the spots. With this construction, it is possible to detect the lights from the spots formed on the analysis chip surely.

It is also preferred that each of said light paths includes a stray lights rejector for rejecting lights from other than the corresponding spots. With this construction, it is possible to conduct the analysis precisely.

It is also preferred that said light path selecting unit is provided plurally and hierarchically. With this construction, even when lots of spots are, it is possible to construct the analysis apparatus and the condenser using only already-existing light path selecting units selecting relatively few light paths without preparing a specifically designed light path selecting unit that can select lots of light paths, which leads to the reduction in costs.

It is also preferred that said light-sensitive detector includes a photomultiplier tube. With this construction, it is possible to achieve both the reduction in costs of the analysis apparatus and the enhanced accuracy of the analysis.

And it is preferred that said lights detected by the light-sensitive detector are at least one type selected from the group consisting of chemiluminescence, electrochemiluminescence, biochemiluminescence, fluorescence, phosphorescence, reflection light and transmitted light.

According to the present invention, it is possible to enhance the positioning accuracy while detecting lights by means of simplifying the position adjusting of the light-sensitive detector and the analysis chip, and also enhance the analysis accuracy by means of stabilizing the state of holding the samples easily. Furthermore, it is possible to downsize the analysis apparatus by means of omitting a mechanism for driving the analysis chip and the light-sensitive detector.

DESCRIPTION OF THE PREFERRED EMBODIMENTS

In the following, embodiments of the present invention will be described. The present invention is not restricted to the following description, but any modification can be made without departing from the scope of the present invention.

1. First Embodiment

Figure 1:
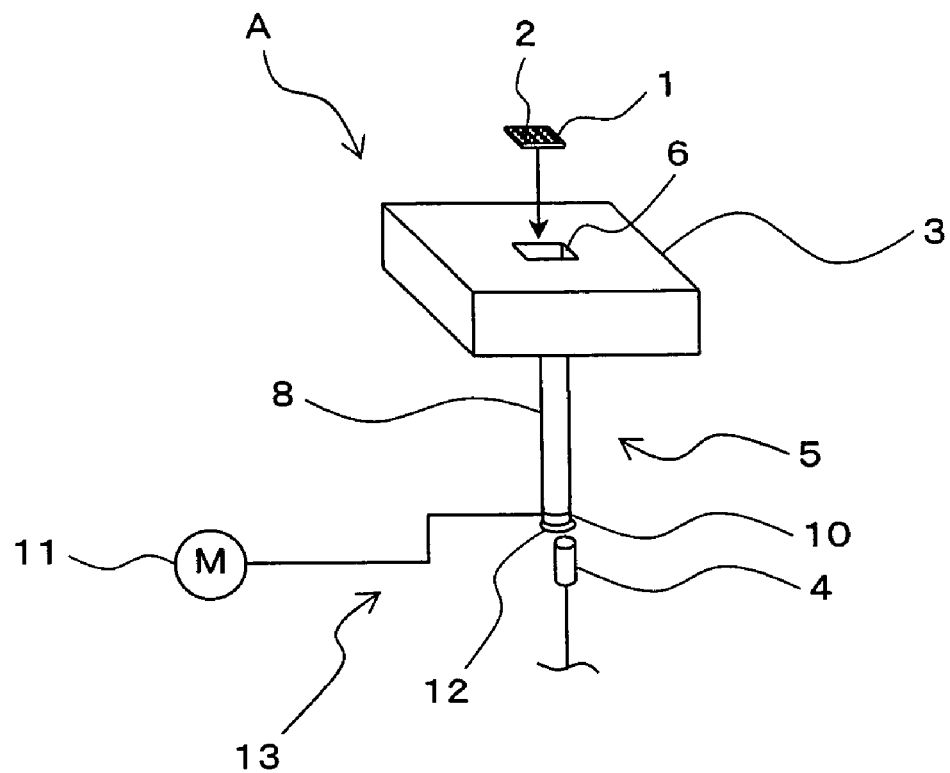
FIG. 1 is a schematic perspective view of an analysis apparatus according to the first embodiment of the present invention.
Figure 2:
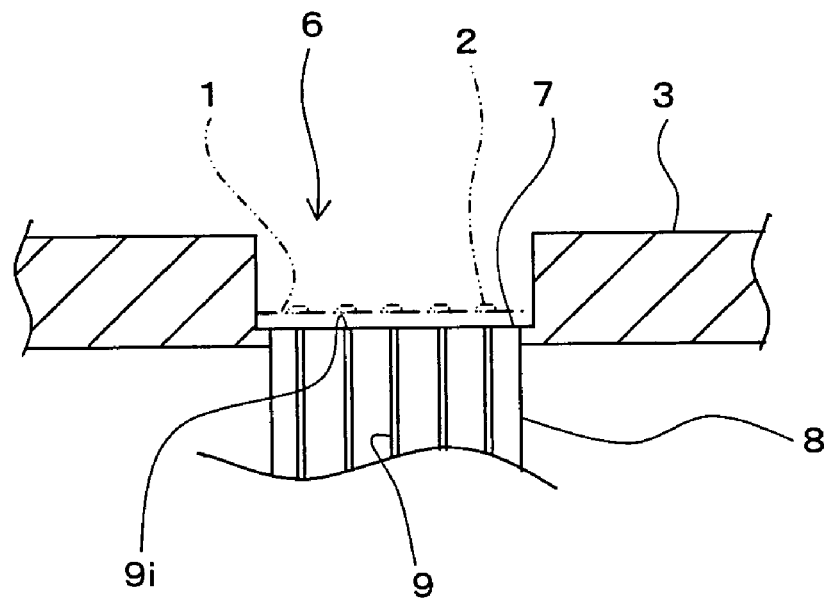
FIG. 2 is a sectional view of a chip holder used in the analysis apparatus according to the first embodiment of the present invention.
Figure 3:
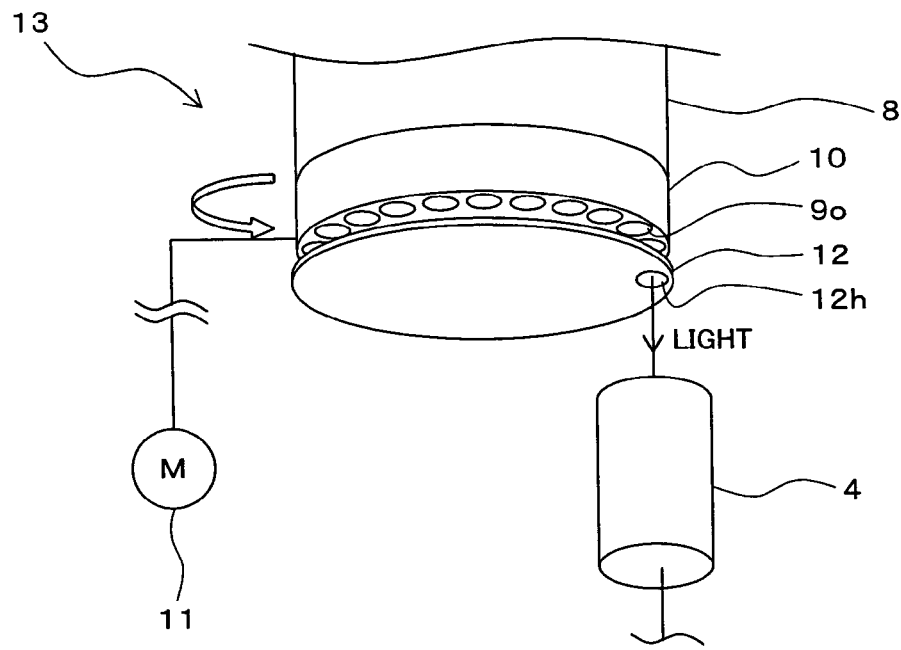
FIG. 3 is an enlarged perspective view of a rotating holder and its surroundings according to the first embodiment of the present invention.
Figure 4:
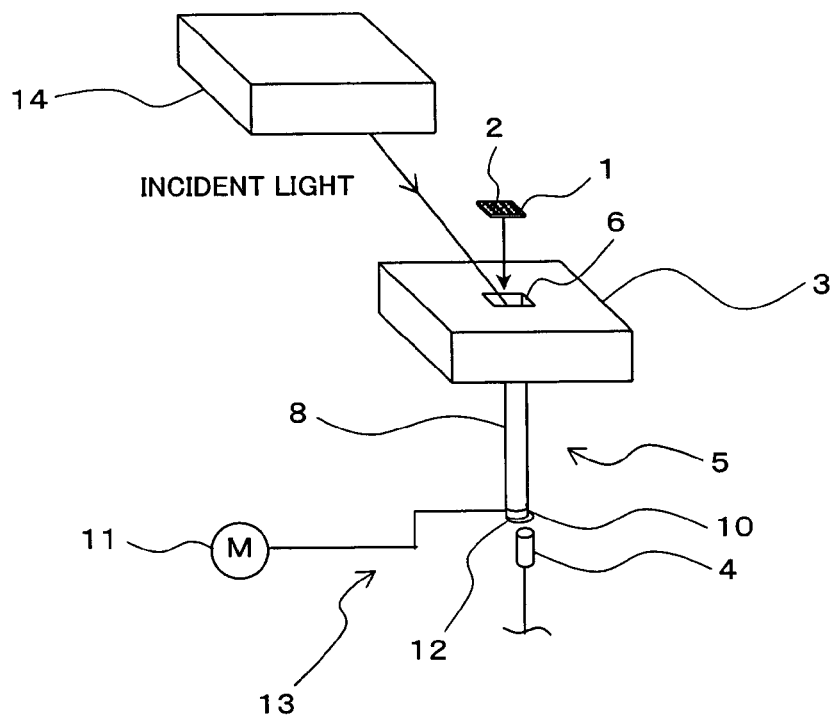
FIG. 4 is a schematic perspective view of an analysis apparatus as a modification of the first embodiment of the present invention.

In the following, the first embodiment of the present invention is described with reference to FIGs. FIGS. 1-4 show the constructions of the embodiment. FIG. 1 is a schematic perspective view of an analysis apparatus according to the first embodiment. FIG. 2 is a sectional view of a chip holder used in the analysis apparatus. FIG. 3 is an enlarged perspective view of a rotating holder and its surroundings. FIG. 4 is a schematic perspective view of the analysis apparatus as a modification of the first embodiment.

The analysis apparatus A shown in FIG. 1 utilizes an analysis chip 1 for detecting lights coming from spots 2 formed plurally on the analysis chip 1. Each spot 2 has a specific material immobilized thereon. In this embodiment, "specific material" means a material that generates chemiluminescence through interaction with a reactant and thus "light from the spot 2" is a light generated as chemiluminescence. The portions of the analysis chip 1 formed with the spots 2 thereon are fabricated with a chemiluminescence permeable material. Therefore, when a light generated from the spots 2, the light can pass through the chip 1 toward the backside or the opposite side to the spots 2 of the chip 1.

As illustrated in FIG. 1, the analysis apparatus A comprises a chip holder 3 for holding the analysis chip 1 while it is used for conducting the analysis and a light-sensitive detector or a photomultiplier tube 4 for detecting the lights from the spots 2 of the analysis chip 1. A selectively light-transmitting unit or condenser 5 is also provided between the chip holder 3 and the photomultiplier tube 4. The condenser 5 transmits lights selectively from the spots 2, formed on the analysis chip 1 held by the chip holder 3, to the photomultiplier tube 4. That is, the lights from the spots 2 on the analysis chip 1 held by the chip holder 3 are transmitted through the condenser 5 and then detected by the photomultiplier tube 4. Pay attention to that the analysis chip 1 is constructed apart from the analysis apparatus A and is placed on the chip holder 3 when it is prepared to use.

The description that "the condenser 5 transmits lights selectively" mentioned above means that the condenser 5 selects the desired spots 2 from all of the spots 2 provided plurally on the analysis chip 1 and transmits the lights, not from the unselected spots 2, but from the selected, or desired, spots 2. Though in this embodiment a single spot 2 is selected as the desired spot 2 just for an example, the condenser 5 may select two or more spots 2 if necessary.

FIG. 2 is a vertical sectional view of the chip holder 3. As illustrated in FIG. 2, a chip place 6 for equipping the analysis chip 1 is formed on the chip holder 3. The analysis is conducted using the analysis apparatus A in a state where the analysis chip 1 is placed on the chip place 6 from upper side. At the bottom of the chip place 6, an opening 7 is formed, through which a light path forming section or a transmission cable 8 mentioned below is inserted.

The condenser 5 includes the transmission cable 8 that forms light paths from the analysis chip 1, which is placed on the chip place 6, to the photomultiplier tube 4. One end of the transmission cable 8 is inserted through the opening 7 of the chip holder 3, thereby the transmission cable 8 can receive the lights from the analysis chip 1. The other end of the transmission cable 8 is disposed at the position where it can output the lights to the photomultiplier tube 4.

The transmission cable 8 includes optical transmission media or optical fibers 9 provided in correspondence with each spot 2 of the analysis chip 1 in number. Each optical fiber 9 has an end 9i (hereinafter called a light-inputting end 9i, whenever it is necessary) for receiving the light from each of the spots, and the other end 9o (hereinafter called a light-outputting end 9o, whenever it is necessary) for outputting the light to the light-sensitive detector. Thus, the lights are transmitted through the optical fibers 9, thereby the light paths are formed within the transmission cable 8.

Each light-inputting end 9i of the optical fiber 9 is disposed at the position corresponding to each spot 2 of the analysis chip 1, which makes it possible for each light-inputting end 9i to receive the light from each corresponding spot 2, in case the analysis chip 1 is placed on the chip holder 3. More specifically, each light-inputting end 9i of the optical fiber 9 is disposed at such a close position to each portion fabricated with a light-permeable material, which is at opposite side to each spot 2 on the analysis chip 1, as to receive the light from the spot 2.

As illustrated in FIG. 3, the condenser 5 has a light-outputting end holder or a rotating holder 10, at the other end of the transmission cable 8, for keeping the light-outputting ends 9o of the optical fibers 9 on the circumference of the same circle. More specifically, the rotating holder 10 is formed in circular shape and the light-outputting ends 9o of the optical fibers 9 are disposed on the edge thereof, thereby the light-outputting ends 9o of the optical fibers 9 are kept on the circumference of the same circle or the rotating holder 10.

The rotating holder 10 has a rotation axis (not shown in FIGs.) in the center of the circular shape, and the holder 10 is able to rotate about the rotation axis. The condenser 5 has a light-outputting end moving unit or a motor 11 that drives the rotating holder 10 to rotate about the rotation axis. With the rotation of the rotating holder 10, the light-outputting ends 9o of the optical fibers 9 move along the circumference of the same circle centering the rotation axis, without getting out of the circumference.

The condenser 5 has also a light-shielding plate 12 formed a hole 12h thereon, located to face the rotating holder 10. The light-shielding plate 12 is constructed in such a manner as to let the light from the light-outputting end 9o of the optical fiber 9 located to the very front of the hole 12h pass through and to shield the lights from the other light-outputting ends 9o.

The photomultiplier tube 4 is disposed at the position where the photomultiplier tube 4 can receive the light through the hole 12h of the light-shielding plate 12, more specifically, the position in front of the hole 12h of the light-shielding plate 12. That is, the photomultiplier tube 4 is disposed to face the light-outputting end 9o which locates in front of the hole 12h through the hole 12h therebetween, to thereby the light from the light-outputting end 9o placed in front of the hole 12h is input into the photomultiplier tube 4 surely.

As mentioned above, the apparatus A is constructed in such a manner that the rotating holder 10, driven to rotate by the motor 11, selects one light-outputting end 9o of the optical fiber 9 corresponding to the desired spot 2 to locate in front of the hole 12h of the light-shielding plate 12, and that the light output from the light-outputting end 9o which is in front of the hole 12h is detected by the photomultiplier tube 4. Thus, the rotation of the rotating holder 10 moves the light-outputting end 9o of the optical fiber 9 into the position where an optical path, formed by the light from the desired spot 2 to the photomultiplier tube 4, is established. That is, the rotating holder 10, the motor 11, and the light-shielding plate 12 form the light path selecting unit 13 for transmitting lights selectively from the desired spot 2a to the photomultiplier tube 4 by means of selecting the light path.

When the analysis is conducted using the analysis apparatus A of this embodiment, having the construction described above, the analysis chip 1 is equipped on the chip place 6 of the chip holder 3 firstly. Pay attention to that the specific materials should be immobilized on the spots 2 of the analysis chip 1 in advance.

Then the specimens are touched on the spots 2 on the analysis chip 1 in the state where the analysis chip 1 is held by the chip holder 3. If the specimens contain reactants, they interact with the specific materials to emit lights from the spot 2 by chemiluminescence. In this embodiment, a sample means a specimen-touched specific material, thus the sample emits a light if the specimen contains a reactant, but the sample does not emit a light if the specimen does not contain a reactant.

When the spot 2 generates the light by chemiluminescence emitted from the sample, the light passes through the analysis chip 1 to the backside thereof and is received by the light-inputting end 9i of the corresponding optical fiber 9. The received light then goes through the optical fiber 9 and is output from the light-outputting end 9o of the optical fiber 9.

The rotating holder 10 is then driven to rotate by the motor 11 to control the position of the light-outputting end 9o of the optical fiber 9. And the rotating holder 10 moves the light-outputting end 9o of the optical fiber 9 corresponding to the desired spot 2 (hereinafter called the desired light-outputting end 9o, if necessary) selectively to the position where the light from the light-outputting end 9o through the hole 12h can be detected by the photomultiplier tube 4, specifically, to the position where the light-outputting end 9o faces to the hole 12h of the light-shielding plate 12. In other words, the rotating holder 10 moves the desired light-outputting end 9o selectively to the position where a light path from the desired spot 2 to the photomultiplier tube 4 is established. With this construction, the light output from the desired light-outputting end 9o passes through the hole 12 and is detected by the photomultiplier tube 4.

At this time, the lights other than that from the desired light-outputting end 9o, or the light transmitted by the optical fiber 9 corresponding to the spots 2 other than the desired spot 2 are never detected by the photomultiplier tube 4 because they are not located to the position where they can be detected by the photomultiplier tube 4, or the position in front of the hole 12h. Furthermore, the light-shielding plate 12 prevents the lights from other than the desired spot 2 from radiating through the light-outputting ends 9o and getting to be stray lights that may cause a disturbance of detecting the light from the desired spot 2.

According to the analysis apparatus A of the present embodiment described above, the light from the desired spot 2 on the analysis chip 1 formed with the plurality of the spots 2 can be detected without any motion of the analysis chip 1 or the photomultiplier tube 4. This construction leads to the advantage that the omission of the mechanism for driving the analysis chip 1 and the photomultiplier tube 4 causes the downsizing of the analysis apparatus A.

In addition, because light detection can be carried out keeping the analysis chip 1 to be fixed, it is possible to prevent the specimens, the specific materials, or the other materials that are not the target of the analysis from moving or being mixed unexpectedly occurred by the motion of the analysis chip 1. This leads to the advantage of stabilized and accurate detection of the lights. The fixing of the analysis chip 1 and the photomultiplier tube 4 can also get rid of the vibrations occurred by driving of them, which also leads to the prevention of the mechanical vibrations noise, the electric noise, or the displacements of the optical axis. Consequently, the light-detecting efficiency and the analysis accuracy can be highly enhanced.

Further, because the lights can be transmitted selectively from the desired spots 2 to the photomultiplier tube 4 with such a simple construction as selecting the light paths, it is possible to construct the apparatus A highly simply, which has thus the advantage of downsizing of the apparatus A and simplifying the operation thereof.

Further, with the fact that the light path is constructed by a optical transmission medium, or an optical fiber 9 for example, provided with a light-inputting end 9i and a light-outputting end 9o, the light from the spot 2 on the analysis chip 1 can be transmitted to the photomultiplier tube 4 surely.

Further, with the construction of the light-outputting ends 9o of the optical fibers 9 being arranged on the circumference of the same circle, the detection of the light from the desired spot 2 can be carried out by simple control and thus very quickly. More specifically, in order to detect the light from the desired spot 2 in the conventional analysis apparatus, it is necessary for either the analysis chip 1 or the photomultiplier tube 4 to move in a plane for the requirements of scanning the analysis chip 1 on each spot 2. In other words, the placement control in both vertical and horizontal directions are required conventionally for the photomultiplier tube 4 to be located at the position where it can detect the light from the spot 2 according to the arrangement of the spots 2. But, according to the present embodiment of the analysis apparatus A, with just the control of the rotation angle of the rotating holder 10, the light can be detected from the desired spot 2 easily, having no relation to the arrangement of the spots 2 on the analysis chip 1. Moreover, the control is so easy that the time required for selecting the light paths is shortened and thus the light from the desired spot 2 can be detected quickly.

Further, the use of the photomultiplier tube 4 as the light-sensitive detector can cost lower than that of other conventional means like a CCD camera, as well as can conduct the analysis more precisely.

Although the analysis apparatus A according to the first embodiment of the present invention has been described particularly, it is to be understood that modifications and variations are possible if necessary.

For one example, though an instance of the light from the spot 2 being generated by chemiluminescence was described in the present embodiment, the light from the desired spot 2 is not restricted to chemiluminescence, but other types of lights emitted by other mechanisms such as electrochemiluminescence or biochemiluminescence can be detected. For further example, any other types of lights that are not generated by emission can be detected, such as lights induced by excitation like fluorescence and phosphorescence, a reflection light reflected on the spot 2, transmitted light passed through the spot 2 or the like, as far as they are transmitted from the spot 2 of the analysis chip 1 to the photomultiplier tube 4. When an incident light is needed to be applied on the analysis chip 1 for detecting lights induced by excitation, reflection lights or transmitted lights, a light source 14 for applying the incident light on the analysis chip 1 held by the chip holder 3 may be provided, as illustrated in FIG. 4. In FIG. 4, the components that are substantially the same as those in FIG. 1-3 have the same reference letter as in FIG. 1-3.

2. Second Embodiment

Figure 5:
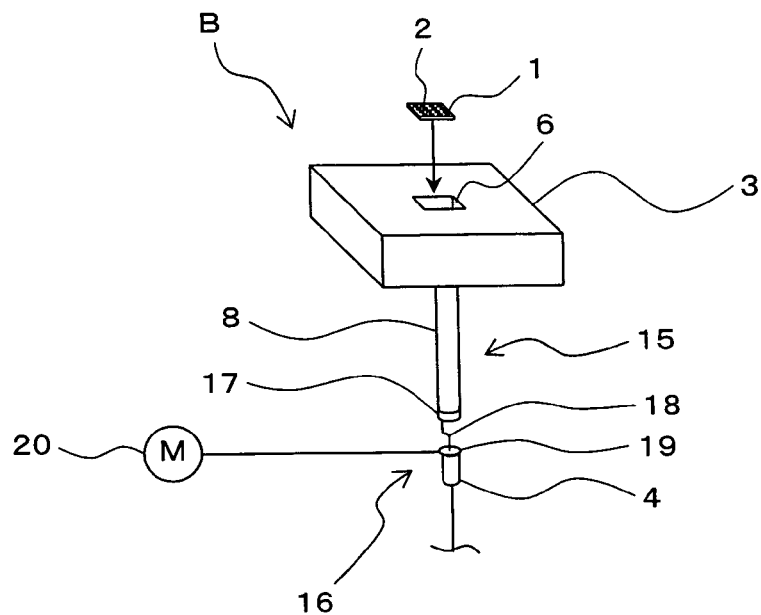
FIG. 5 is a schematic perspective view of an analysis apparatus according to the second embodiment of the present invention.
Figure 6:
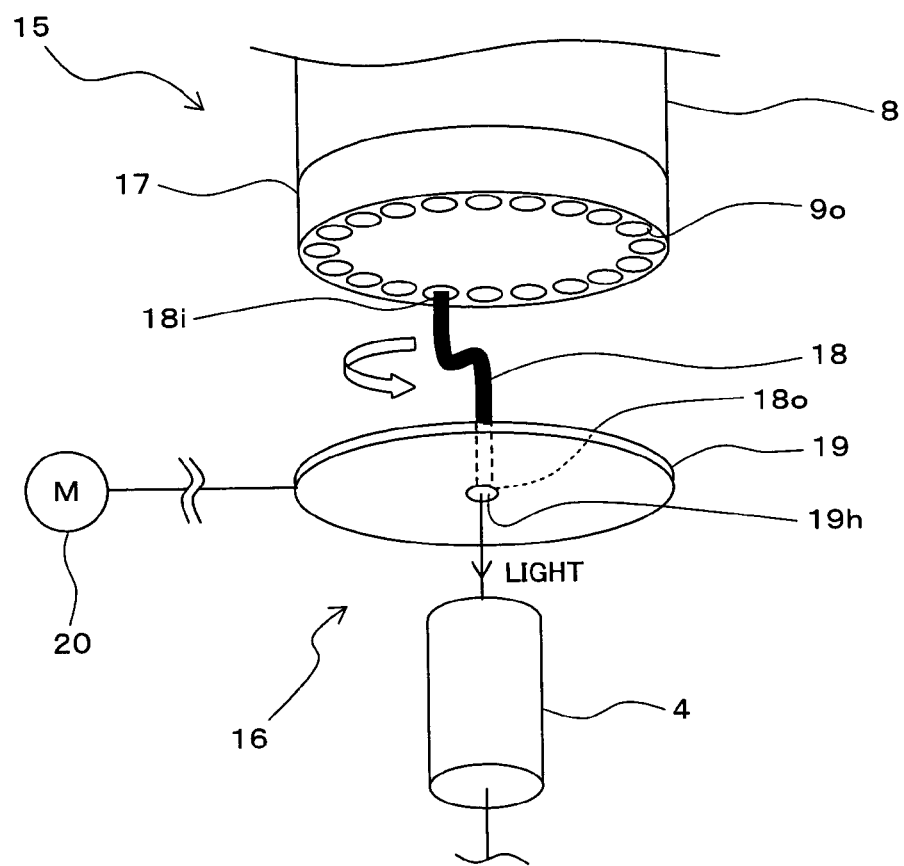
FIG. 6 is an enlarged perspective view of a crank fiber and its surroundings according to the second embodiment of the present invention.

In the following, the second embodiment of the present invention is described with reference to FIGs. FIGS. 5 and 6 show the constructions of the embodiment. FIG. 5 is a schematic perspective view of the analysis apparatus. FIG. 6 is an enlarged perspective view of a crank fiber and its surroundings. In FIGS. 5 and 6, components that are substantially the same as those in FIGS. 1-4 have the same reference letter as in FIGS. 1-4.

As illustrated in FIG. 5, the analysis apparatus B has the same basic constructions as the analysis apparatus A described in the first embodiment such as a chip holder 3 for holding the analysis chip 1 and a light-sensitive detector or a photomultiplier tube 4. The lights from the spots 2 on the analysis chip 1 held by the chip holder 3 are detected by the photomultiplier tube 4. A condenser 15 is provided to the analysis apparatus B in place of the condenser 5 to the analysis apparatus A. The other components of the apparatus B are similar to those of the apparatus A.

More specifically, the condenser 15 is provided between the chip holder 3 and the photomultiplier tube 4 to transmit the lights from the spots 2 on the analysis chip 1 to the photomultiplier tube 4. The condenser 15 or the selectively light-transmitting unit has a transmission cable 8 comprising optical fibers 9, similarly to the condenser 5 of the apparatus A. A light path selecting unit 16 is provided to the condenser 15 of the analysis apparatus B in place of the light path selecting unit 13. The light path selecting unit 16 consists of a light-outputting end holder or a circular holder 17, a selectively optical transmission medium or a crank fiber 18, a light-shielding plate 19, and a selected-light inputting end moving unit or a motor 20.

The light path selecting unit 16 is described more particularly in the following.

As shown in FIG. 6, the condenser 15 has the circular holder 17, at the other end of the transmission cable 8 (the opposite end to the chip holder 3), for keeping the light-outputting ends 9o of the optical fibers 9 on the circumference of the same circle, similar to the first embodiment. More specifically, the circular holder 17 is formed in circular shape and the light-outputting ends 9o of the optical fibers 9 are disposed on the peripheral part of the circular shape, thereby the light-outputting ends 9o of the optical fibers 9 being kept on the circumference of the same circle, or the shape of the circular holder 17. However, the circular holder 17 is fixed, or not rotatable, in contrast to the first embodiment.

The condenser 15 has a light-shielding plate 19 formed a hole 19h thereon, located to face the circular holder 17. The hole 19h is disposed at the front of the center of the circular holder 17, having a circular shape. The crank fiber 18 is inserted into the hole 19h.

The crank fiber 18, which is an optical fiber formed in the shape of a crank, has a selected-light inputting end or a light-inputting end 18i for receiving the light and a selected-light outputting end or a light-outputting end 18o for outputting the light. The light-outputting end 18o, inserted into the hole 19h of the light-shielding plate 19, is a rotation axis about which the crank fiber 18 rotates. When the crank fiber 18 is rotated, the light-inputting end 18i of the crank fiber 18 moves along the circumference of the circular holder 17 where the light-outputting ends 9o of the optical fibers 9 are disposed.

The condenser 15 has a motor 20 that is connected to the crank fiber 18 and that drives the crank fiber 18 to rotate about the light-outputting end 18o.

The photomultiplier tube 4 is disposed at the position where it can receive the light from the light-outputting end 18o of the crank fiber 18, in other words, the position in front of the hole 19h of the light-shielding plate 19. As a result, the photomultiplier tube 4 can detect the light from the light-outputting end 18o of the crank fiber 18 surely. The lights output from other than the light-outputting end 18o of the crank fiber 18 are shielded by the light-shielding plate 19 so as not to reach the photomultiplier tube 4.

As mentioned above, the apparatus B is constructed in such a manner as the following. That is, the rotation of the crank fiber 18, driven by the motor 20, moves the light-inputting end 18i of the crank fiber 18 along the light-outputting ends 9o of the optical fibers 9. Then, the light-inputting end 18i of the crank fiber 18, located selectively to face one of the light-outputting ends 9o of the optical fibers 9 (more specifically, the light-outputting end 9o of the optical fiber 9 corresponding to the desired spot 2), receives the light output from the light-outputting ends 9o of the optical fiber 9. And finally the light output from the light-outputting end 18o of the crank fiber 18 is detected by the photomultiplier tube 4. Thus, the rotation of the crank fiber 18 moves the light-inputting end 18i of the crank fiber 18 selectively into the position where an optical path, formed by the light from the desired spot 2 to the photomultiplier tube 4, is established. Consequently, the crank fiber 18, the light-shielding plate 19, and the motor 20 form the light path selecting unit 15 for transmitting lights selectively from the desired spot 2 to the photomultiplier tube 4 by means of selecting the light path.

When the analysis is conducted using the analysis apparatus B of this embodiment, having the construction described above, similarly to the first embodiment, the analysis chip 1 is equipped on the chip place 6 of the chip holder 3 and the specimens are touched on the spots 2 of the analysis chip 1 firstly.

When the spot 2 generates the light by chemiluminescence emitted from the sample through the touch of the specimen and the specific material, similarly to the first embodiment, the light passes through the analysis chip 1 to the backside thereof and is received by the light-inputting end 9i of the corresponding optical fiber 9. The received light then goes through the optical fiber 9 and is output from the light-outputting end 9o of the optical fiber 9.

The crank fiber 18 is then driven to rotate by the motor 20, so as to adjust the light-inputting end 18i of the crank fiber 18 and to move the light-inputting end 18i of the crank fiber 18 selectively to the position where the light from the desired light-outputting end 9o can be received, more specifically, to the position facing to the desired light-outputting end 9o. In other words, the crank fiber 18 moves the light-inputting end 18i of the crank fiber 18 selectively to the position where a light path from the desired spot 2 to the photomultiplier tube 4 is established. With this construction, the light output from the desired light-outputting end 9o passes through the crank fiber 18 and is detected by the photomultiplier tube 4.

At this time, the lights other than that from the desired light-outputting end 9o, or the lights output from the spots 2 that are other than the desired spot 2, are never detected by the photomultiplier tube 4 because they cannot reach the photomultiplier tube 4. Furthermore, the light-shielding plate 19 prevents the lights transmitted through the optical fibers 9 corresponding to other than the desired spot 2 from being radiated through the light-outputting ends 9o of the optical fibers 9 and getting to be stray lights that may cause a disturbance of detecting the light from the desired spot 2.

According to the analysis apparatus B of the present embodiment described above, the light from the desired spot 2 on the analysis chip 1 can be detected without any motion of the analysis chip 1 or the photomultiplier tube 4. Thus, the light detection can be conducted with the analysis chip 1 and the photomultiplier tube 4 fixed. Thereby, it is possible to omit the mechanism for driving them and thus to downsize the analysis apparatus B.

In addition, the fixing of the analysis chip 1 and the photomultiplier tube 4 can also get rid of the vibrations occurred by driving of them, which also leads to the prevention of the mechanical vibration noise, the electric noise, or the displacement of the optical axis. Consequently, the light-detecting efficiency and the analysis accuracy can be highly enhanced.

Further, with such a simple construction that the light-outputting ends 9o of the optical fibers 9 are disposed on the circumference of the same circle and the light path is selected by the crank fiber 18, the detection of the light from the desired spot 2 can be carried out easily by a simple control and thus very quickly. That is, according to the present embodiment of the analysis apparatus B, with just the control of the rotation angle of the crank fiber 18, the light can be detected from the desired spot 2 easily, having no relation to the arrangement of the spots 2 on the analysis chip 1. Moreover, the control is so easy that the time required for selecting the light paths is shortened and thus the light from the desired spot 2 can be detected quickly.

The other operations and effects similar to the first embodiment can be also achieved in the present embodiment.

Also similarly to the first embodiment, it is to be understood that modifications and variations are possible if necessary.

For one example, any other types of lights such as emitted lights by other mechanisms like electrochemiluminescence or biochemiluminescence can be detected by the analysis apparatus B, as well as lights induced by excitation like fluorescence and phosphorescence, reflection lights reflected on the spot 2, and transmitted lights passed through the spot 2. When an incident light is necessary for the analysis, a light source 14 for the incident light may be provided, as illustrated in FIG. 4.

3. Third Embodiment

Figure 7:
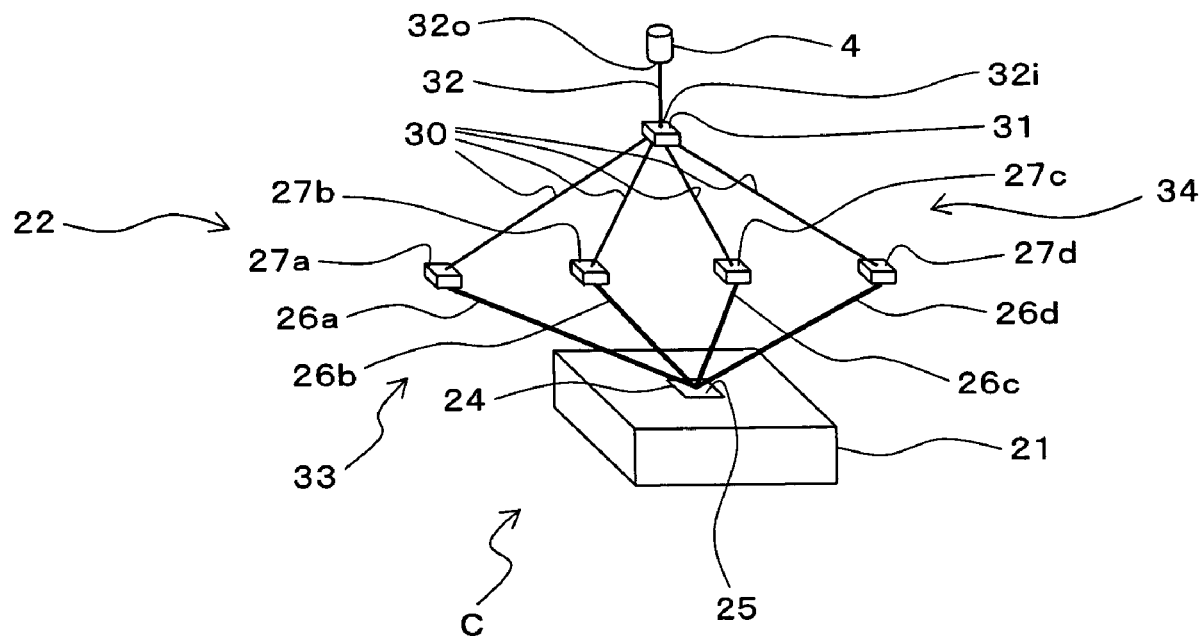
FIG. 7 is a schematic perspective view of an analysis apparatus according to the third embodiment of the present invention.
Figure 8:
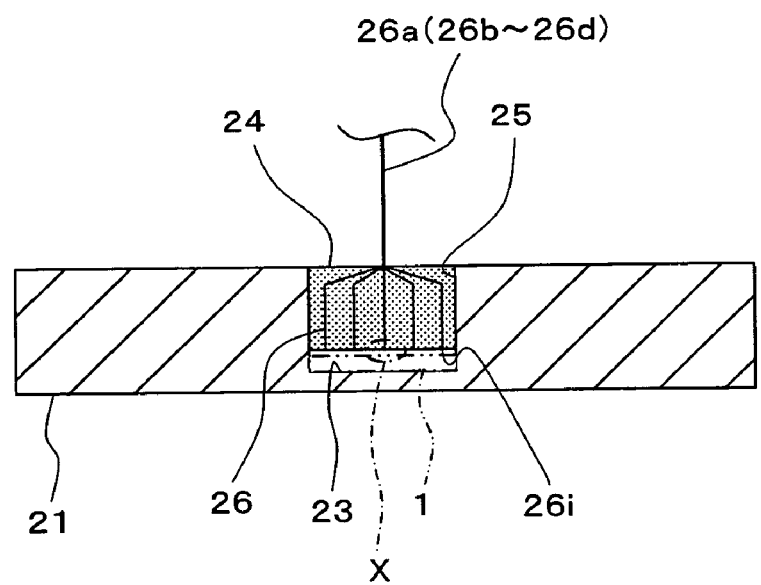
FIG. 8 is a vertical sectional view of a chip holder used in the analysis apparatus according to the third embodiment of the present invention.
Figure 9:
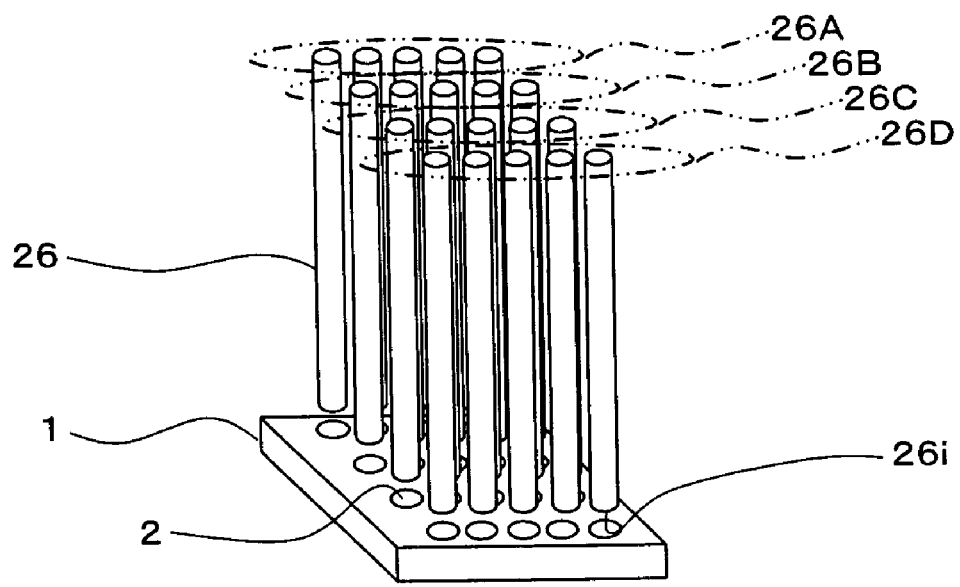
FIG. 9 is a perspective view illustrating a combination of optical fibers used in the analysis apparatus according to the third embodiment of the present invention.
Figure 10:
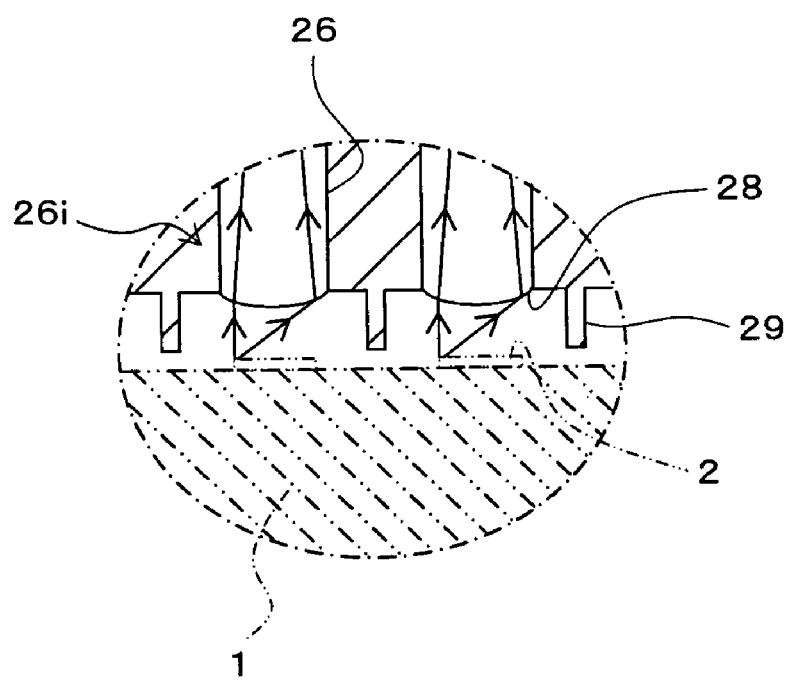
FIG. 10 is an enlarged sectional view of the portion X of FIG. 8.

In the following, the third embodiment of the present invention is described with reference to FIGs. FIGS. 7-15 show the constructions of the embodiment. FIG. 7 is a schematic perspective view of the analysis apparatus. FIG. 8 is a vertical sectional view of a chip holder used in the analysis apparatus. FIG. 9 is a perspective view illustrating schematically a combination of optical fibers used in the analysis apparatus. FIG. 10 is an enlarged sectional view of the portion X of FIG. 8. FIGS. 11-15 are schematic perspective views of selecting units. In FIGS. 7-15, components that are substantially the same as those in FIGS. 1-6 have the same reference letter as in FIGS. 1-6.

The analysis apparatus C shown in FIG. 7, similar to the apparatus A and B described in the first and second embodiments, detects lights, using an analysis chip 1, coming from spots 2 formed plurally on the analysis chip 1. Each spot 2 has a specific material immobilized thereon.

The analysis apparatus C has the same basic constructions as the analysis apparatus A and B described in the first and second embodiments such as a chip holder 21 for holding the analysis chip 1 and a light-sensitive detector or a photomultiplier tube 4. The lights from the spots 2 on the analysis chip 1 held by the chip holder 21 are detected by the photomultiplier tube 4. A condenser 22 is provided between the chip holder 21 and the photomultiplier tube 4, and the condenser 22 transmits lights from the spots 2 on the analysis chip 1 to the photomultiplier tube 4.

The construction of the analysis apparatus C is described more particularly in the following.

FIG. 8 is a vertical sectional view of the chip holder 21. As illustrated in FIG. 8, a chip place 23 is formed inside of the chip holder 21 of the analysis apparatus C. When the analysis is conducted used with apparatus C, the analysis chip 1 is inserted through the chip entrance (not shown in FIGs.) formed on the lateral side of the chip holder 21 and placed on the chip place 23. At the top of the chip place 23, an opening 25 is formed, through which a light-receiving unit 24 mentioned below is inserted.

The condenser 22 comprises a light-selecting unit, or optical fibers 26 (optical transmission media) and selecting units 27a-27d. Each optical fiber 26 is provided to be corresponding to each spot 2 of the analysis chip 1 and has a light-inputting end 26i for receiving the light and a light-outputting end 26o for outputting the light. Thus each optical fiber 26 forms each light path in this embodiment.

Each light-inputting end 26i of the optical fiber 26 is fixed to the light-receiving unit 24 inserted in the opening 25. The light-receiving unit 24 is formed in shape fitted to the opening 25 of the chip holder 21. The light-receiving unit 24 keeps each light-inputting end 26i of the optical fibers 26 to be located at the upper front of each corresponding spot 2, thereby each light-inputting end 26i of the optical fibers 26 can receive the light from each corresponding spot 2, as illustrated in FIG. 9.

As shown in FIG. 10, focusing lenses 28 are formed at the respective light-inputting ends 26i of optical fibers 26. FIG. 10 is an enlarged sectional view of the portion X of FIG. 8. As shown in this illustration, each light-inputting end 26i of the optical fibers 26 has a focusing lens 28, for each optical fiber 26 to be able to focus the light from the corresponding spot 2, as illustrated with the arrows in FIG. 10.

Each light-inputting end 26i of the optical fiber 26 has a stray lights rejector or a light-shielding wall 29 around it. More specifically, each light-shielding wall 29 provided between each adjacent light-inputting ends 26i rejects lights from other than the corresponding spot 2, especially from the adjacent spots 2. In other words, the apparatus C is such constructed as to be possible to reject the stray lights from the spots 2 other than the corresponding spot 2 owing to the fact that the optical fibers 26 have the light-shielding walls 29.

As shown in FIG. 9, a plurality of optical fibers 26 are divided into the groups 26A-26D inside the light-receiving unit 24 and each group 26A-26D of the optical fibers 26 includes a bundle of five optical fibers 26a-26d. Although an example of twenty optical fibers 26 are divided into the groups 26A-26D, each of which is bundled to form the optical fiber bundles 26a-26d in FIG. 9, the way of the grouping is not restricted particularly.

Each bundle 26a-26d of the optical fibers 26 is connected to each selecting unit 27a-27d so as to output the light from each light-outputting end 26o of the optical fibers 26 to the selecting unit 27a-27d. The selecting units 27a-27d, described more specifically below, output the light from the desired spot 2 selectively.

Each selecting unit 27a-27d has an optical fiber 30 on the outputting side thereof. Each optical fiber 30 has a light-inputting end 30i for receiving the light and a light-outputting end 30o for outputting the light. The light-inputting ends 30i of the optical fibers 30 are connected to the selecting units 27a-27d and the light-outputting ends 30o are connected to a selecting unit 31. Thus, the lights received at the light-inputting ends 30i are output from the light-outputting ends 30o to the selecting unit 31. The selecting units 31, described more specifically below, has a similar construction to the selecting units 27a-27d except for having only four optical fibers connected into the inputting side thereof.

The selecting unit 31 has an optical fiber 32 on the outputting side thereof. The optical fiber 32 has a light-inputting end 32i for receiving the light and a light-outputting end 32o for outputting the light. The light-inputting end 32i of the optical fibers 32 is connected to the selecting unit 31 and the light-outputting end 32o is located at such position that the photomultiplier tube 4 can detect the light. Thus, the light received at the light-inputting end 32i is output from the light-outputting end 32o and is detected by the photomultiplier tube 4.

That is, the optical fibers 26, 30, 32 serves as the light paths, while the light-receiving unit 24 and the optical fibers 26, 30, 32, including groups 26a-26d, turn to be the light path forming section 33 that form the light paths from the spots 2 on the analysis chip 1 to the photomultiplier tube 4. The selecting units 27a-27d, 31 turn to be the light path selecting unit for transmitting the lights selectively from the desired spots 2 to photomultiplier tube 4 by means of selecting the light paths.

In addition, the condenser 22 has a hierarchical structure of the light path selecting unit 34, which means that the selecting units 27a-27d form the upper hierarchy of the light path selecting unit 34 or the upstream selecting unit, and the selecting unit 31 form the lower hierarchy of the light path selecting unit 34 or the downstream selecting unit. Thus, the light transmitted selectively to the selecting unit 31 by means of selecting the light paths using the selecting units 27a-27d is then transmitted selectively to the photomultiplier tube 4 by means of selecting the light paths using the selecting unit 31. Consequently, selecting the light paths can be carried out in steps that can be divided into multiple, hierarchical stages.

In the following, the selecting units 27a-27d, 31 will be described specifically, adopting the unit 27a for an example.

The selecting unit 27a has a bundle of five optical fibers 26a belonging to the group 26A on its inputting side and a single optical fiber 30 on its outputting side. The construction of the selecting unit 27a may be changed in any ways as far as it can transmit the lights from the desired light-outputting ends 26o, among all of the light-outputting ends 26o of the optical fibers 26, selectively into the light-inputting end 30i of the optical fiber 30.

Figure 11:
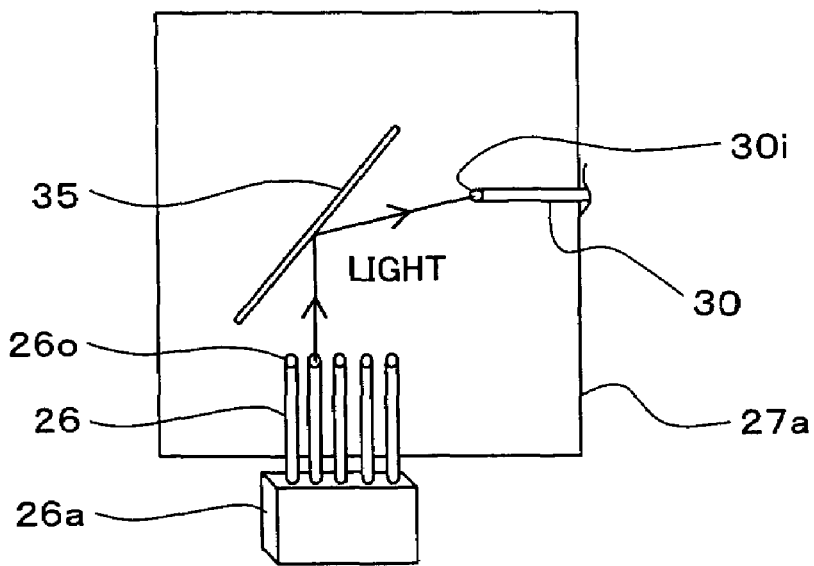
FIG. 11 is a schematic perspective view of a selecting unit with a Garvano mirror, used in the analysis apparatus according to the third embodiment of the present invention.

The construction of the selecting unit 27a of this embodiment is illustrated in FIG. 11. The selecting unit 27a has a Garvano mirror arranged to be rotatable around the rotation axis (not shown in FIGs.). The light output from the light-outputting end 26o of the optical fiber 26 is reflected by the Garvano mirror 35 and received at the light-inputting end 30i of the optical fiber 30. Thus, the selecting unit 27a can select the light from the desired light-outputting end 26o among those from a plurality of light-outputting ends 26o so as to transmit it to the light-inputting end 30i by means of adjusting the rotation angle of the Garvano mirror 35. In other words, the selecting unit 27a selects the light path so as to establish an optical path from the desired spot 2 to the photomultiplier tube 4 by the rotation of the Garvano mirror 35.

The selecting units 27b-27d are of similar constructions to the selecting unit 27a, as mentioned in the above description, which means they also can select the light path for establishing an optical path formed by the light from the desired spot 2 to the photomultiplier tube 4. The selecting units 31 has also a similar construction to the selecting units 27a, that is, it can select the light path for establishing an optical path formed by the light from the desired spot 2 to the photomultiplier tube 4, but it has only four optical fibers 30 connected into the inputting side thereof.

When the analysis is conducted using the analysis apparatus C of this embodiment, having the construction described above, the analysis chip 1 is equipped on the chip place 25 of the chip holder 21 firstly. Pay attention to that the specific materials should be immobilized on a plurality of, or twenty in this embodiment as shown in FIG. 9, spots 2 of the analysis chip 1 in advance.

Then the specimens are touched on the spots 2 on the analysis chip 1 in the state where the analysis chip 1 is held by the chip holder 21. Similar to the first and second embodiments, a sample means a specific material touched by a specimen. If the specimen contains reactants, the corresponding spot 2 generates a light as chemiluminescence on its touch with the specific material.

When the spot 2 emits a light, the light is received by the light-inputting end 26i of the corresponding optical fiber 26. Owing to the fact that each five of the optical fibers 26 is collected to form the bundle 26a-26d and each bundle 26a-26d is connected to each selecting unit 27a-27d, the light received by one of the light-inputting ends 26i is output from the corresponding light-outputting end 26o inside one of the four selecting units 27a-27d.

Inside the selecting units 27a-27d, if it contains the optical fiber 26 corresponding to the desired spot 2, the Garvano mirror 35 rotates to establish the optical path from the desired spot 2 to the photomultiplier tube 4 by reflecting the light from the desired light-outputting end 26o. Consequently, the light from the desired light-outputting end 26o is reflected at the Garvano mirror 35 and then received by the light-inputting end 30i of the optical fiber 30.

The light received at the light-inputting end 30i is transmitted through the optical fiber 30 and then output from the light-outputting end 30o inside the selecting unit 31.

The selecting unit 31, similar to the selecting units 27a, selects the light path to establish the optical path from the desired spot 2 to the photomultiplier tube 4, thereby the light output from the desired light-outputting end 30o being received by the light-inputting end 32i of the optical fiber 32.

The light received by the light-inputting end 32i of the optical fiber 32 is transmitted through the optical fiber 32 and output from the light-outputting end 32o. Then the photomultiplier 4 detects the output light.

According to the analysis apparatus C of the present embodiment described above, the light from the desired spot 2 on the analysis chip 1 can be detected without any motion of the analysis chip 1 or the photomultiplier tube 4. Thus, the light detection can be conducted with the analysis chip 1 and the photomultiplier tube 4 fixed. Thereby, it is possible to omit the mechanism for driving them and thus to downsize the analysis apparatus C.

Furthermore, similar to the first and second embodiments, the stabilized and accurate detection of the lights can be achieved. In addition, the mechanical vibration noise, the electric noise, or the displacement of the optical axis can be prevented. Further, the downsizing of the apparatus C and simplifying the operation thereof can be accomplished.

Further, with the construction that the selecting unit 27a-27d, 31 are provided plurally and hierarchically for carrying out the selection of the light path in multiple steps, even when lots of spots 2 are formed, it is possible to construct the analysis apparatus C using only already-existing selecting units for selecting relatively few light paths without preparing a specifically designed selecting unit for selecting lots of light paths, which leads to the advantage of the reduction in costs. Though in this embodiment the light paths are selected in two steps hierarchically, they can be selected in any more steps.

Further, with the use of the selecting unit 27a-27d, 31, the light can be detected from the desired spot 2 easily. Moreover, the control is so easy that the time required for selecting the light paths is shortened and thus the light from the desired spot 2 can be detected quickly. As an example, it takes less than twenty milliseconds to select the light path when the selecting unit 27a-27d, 31 of this embodiment are used.

Further, with the construction that the light path selecting unit is modularized into the selecting unit 27a-27d, 31, it is possible to enhance replaceability thereof. And the simple constitution of the light path selecting unit makes it possible to reduce the parts count. And also the selecting section, which needs to be a delicate structure, can be surrounded by a somewhat strong construction. These characteristics lead to the advantage of the increase in longevity, the prevention of the malfunction, and the improvement in maintenance-bearing capacity. It is to be understood "maintenance-bearing capacity" means here the capacity for the analysis apparatus of suffering no disadvantage when it is maintenanced, for example, the capacity of preventing the resolution from being lowered even if any vibrations are given by the maintenance operation.

Further, with the construction that each light-inputting end 26i of the optical fibers 26 includes a focusing lens 28, it is possible for the light-inputting end 26i to receive the light from the spot 2 formed on the analysis chip 1 surely and thus for the apparatus C to detect the light from the desired spot 2 steadily.

Further, with the construction that each light-inputting end 26i of the optical fibers 26 has a light-shielding wall 29 for rejecting stray lights, it is possible to detect the light from the spot 2 accurately.

Although the analysis apparatus C according to the third embodiment of the present invention has been described particularly, it is to be understood that modifications and variations are possible if necessary.

For examples, the selecting unit 27a-27d, 31 may be of other constructions as illustrated in FIGS. 12-15. In the following, each modified form of the selecting units 27a-27d, 31 will be described, adopting the unit 27a for an example.

Figure 12:
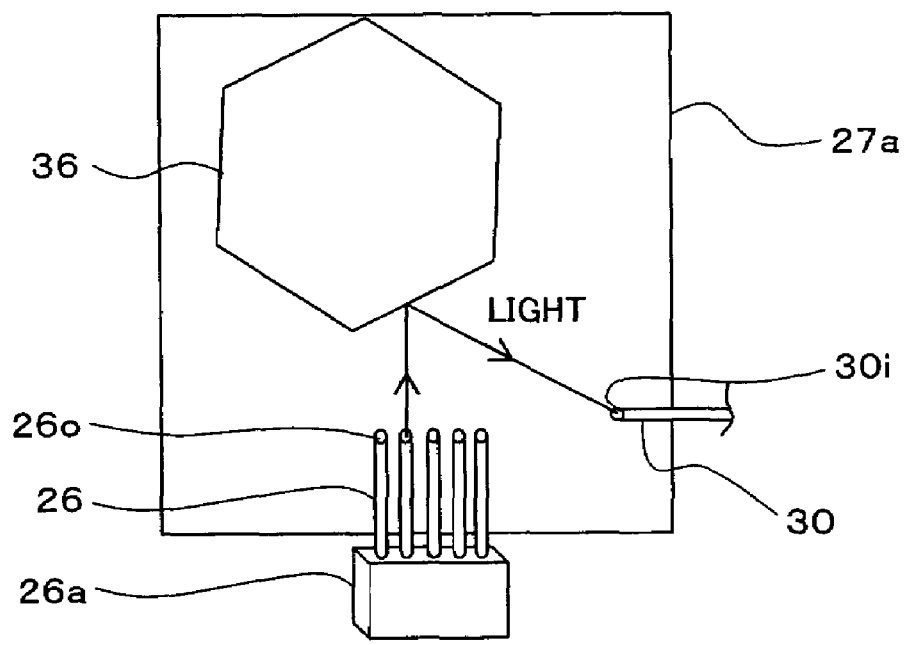
FIG. 12 is a schematic perspective view of a selecting unit with a polygon mirror, used in the analysis apparatus according to the third embodiment of the present invention.

The construction of the selecting unit 27a shown in FIG. 12 is such that a polygon mirror 36 which has a plurality of or six specular surfaces is arranged to be rotatable around the rotation axis (not shown in FIGs.). The light output from the light-outputting end 26o of the optical fiber 26 is reflected by one of the specular surfaces of the polygon mirrors 36 and received at the light-inputting end 30i of the optical fiber 30. Thus, the selecting unit 27a can select the light from the desired light-outputting end 26o among those from a plurality of light-outputting ends 26o so as to transmit it to the light-inputting end 30i by means of adjusting the rotation angle of the polygon mirrors 36. In other words, the selecting unit 27a selects the light path so as to establish an optical path from the desired spot 2 to the photomultiplier tube 4 by the rotation of the polygon mirrors 36. With this construction, the one to one correspondence between the light-inputting end 30i and the light-outputting end 26o is easily realized.

Figure 13:
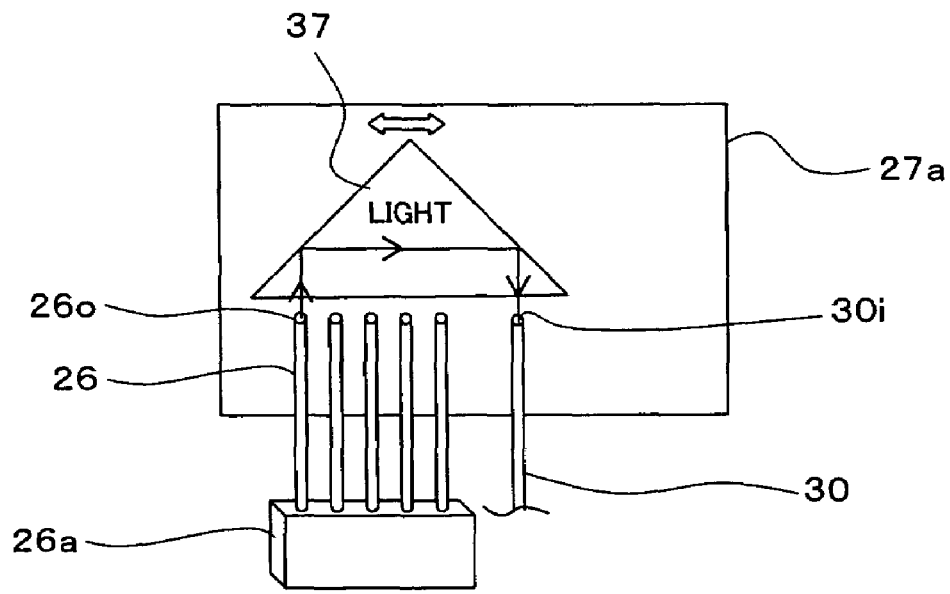
FIG. 13 is a schematic perspective view of a selecting unit with a prism, used in the analysis apparatus according to the third embodiment of the present invention.

The construction of the selecting unit 27a shown in FIG. 13 is such that a prism 37 is arranged to be movable in the horizontal directions of FIG. 13. The light output from the light-outputting end 26o of the optical fiber 26 is reflected by the prism 37 and received at the light-inputting end 30i of the optical fiber 30. Thus, the selecting unit 27a can select the light from the desired light-outputting end 26o among those from a plurality of light-outputting ends 26o so as to transmit it to the light-inputting end 30i by means of adjusting the position of the prism 37. In other words, the selecting unit 27a selects the light path so as to establish an optical path from the desired spot 2 to the photomultiplier tube 4 by the horizontal (in FIG. 13) movement of the prism 37.

Figure 14:
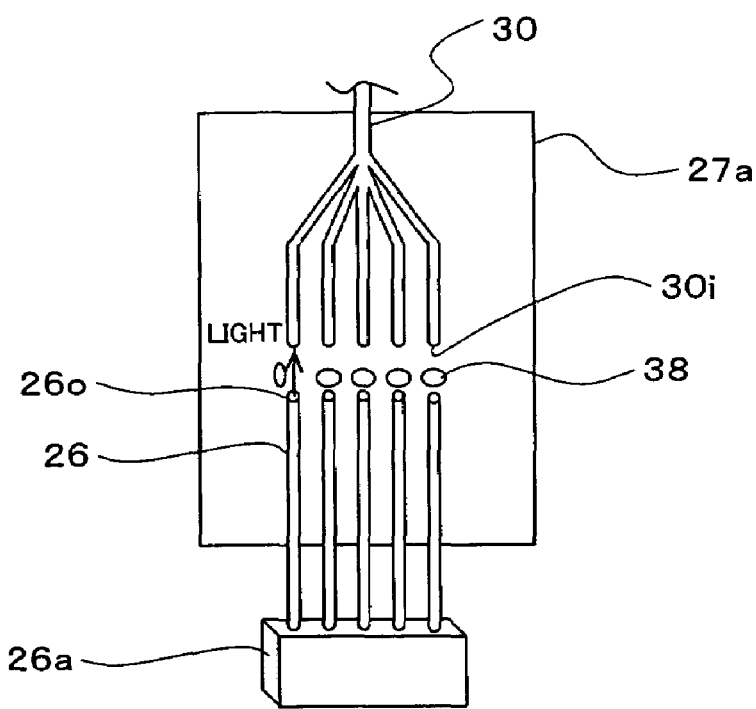
FIG. 14 is a schematic perspective view of a selecting unit with a light shield, used in the analysis apparatus according to the third embodiment of the present invention.

The construction of the selecting unit 27a shown in FIG. 14 is such that light shields 38 are arranged, each of which is able to open and shut each light-outputting end 26o of the optical fibers 26. The light shield 38 is swingable or rotatable about the axis (not shown in FIGs.), and takes an "open position" where it does not shield the light from the light-outputting end 26o and a "close position" where it does shield the light. The inputting end 30i of the optical fiber 30 branches off correspondingly to the light-inputting end 26i, thereby each light-inputting end 30i at each tip of the branches can receive the light from the light-outputting end 26o when the corresponding light shield 38 takes the open position, and can not receive the light when the corresponding light shield 38 in the close position.

Thus, the selecting unit 27a can select the light from the desired light-outputting end 26o among those from a plurality of light-outputting ends 26o so as to transmit it to the light-inputting end 30i by means of adjusting the swing of the light shields 38. In other words, the selecting unit 27a selects the light path so as to establish an optical path from the desired spot 2 to the photomultiplier tube 4 by swinging the light shield to switch between the open position and the close position.

Figure 15A:
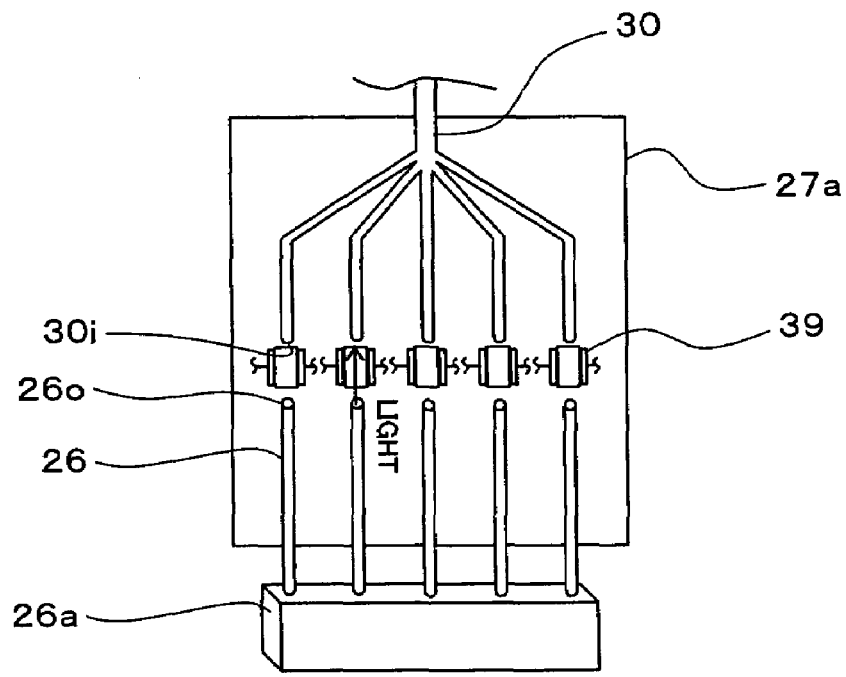
FIG. 15(a) is a schematic perspective view of a selecting unit with a light-shielding unit.

The construction of the selecting unit 27a shown in FIG. 15(a) is such that light path selecting electrical units or light-shielding units 39 are provided, each of which is located in front of each light-outputting end 26o of the optical fibers 26. As shown in FIG. 15(a), each light-shielding unit 39 has a liquid crystal portion 40 filled with liquid crystal and a pair of electrodes 41 arranged on both sides of the liquid crystal portion 40. Each pair of electrodes 41 is supplied a voltage by a power source (not shown in FIGs.) and can apply it to the liquid crystal portion 40. On applying a voltage to the liquid crystal portion 40 by the electrodes 41, the liquid crystal aligns and thus the light can permeate the liquid crystal portion 40. Without a voltage to the liquid crystal portion 40, the liquid crystal does not align and thus the light can not permeate the liquid crystal portion 40. In this example, each liquid crystal portion 40 of the light-shielding unit 39 is located in front of each light-outputting end 26o of the optical fibers 26, and thus the light-shielding units 39 are light-permeable, which means allowing the permeation of the light from the light-outputting end 26o, with a voltage applied from the electrodes 41 to the liquid crystal portion 40 and not light-permeable, which means not allowing the permeation of the light from the light-outputting end 26o, without the voltage.

The inputting end 30i of the optical fiber 30 branches off correspondingly to the light-inputting end 26i, thereby each light-inputting end 30i at each tip of the branches can receive the light from the light-outputting end 26o when the corresponding light-shielding unit 39 is light-permeable, and can not receive the light when the corresponding light-shielding unit 39 is not light-permeable. Thus, the selecting unit 27a can select the light from the desired light-outputting end 26o among those from a plurality of light-outputting ends 26o so as to transmit it to the light-inputting end 30i by means of adjusting the voltage application from the electrodes 41. In other words, the selecting unit 27a selects the light path so as to establish an optical path from the desired spot 2 to the photomultiplier tube 4 by switching the light-shielding unit 39 between the light-permeable state and the not-light-permeable state.

Figure 15B:
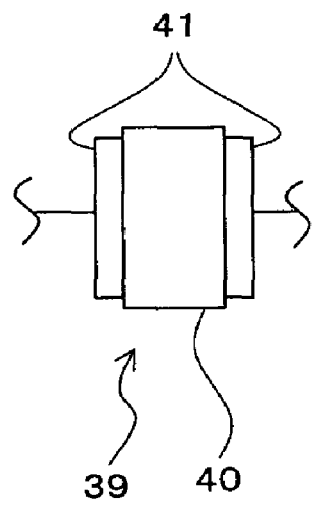
FIG. 15(b) is a schematic view of the light-shielding unit.
Figure 15C:
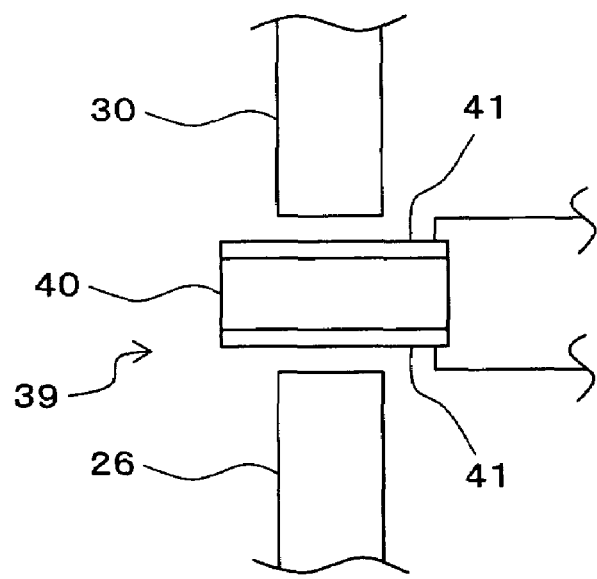
FIG. 15(c) is a schematic view of the light-shielding unit as another form, used in the analysis apparatus according to the third embodiment of the present invention.
Figure 16:
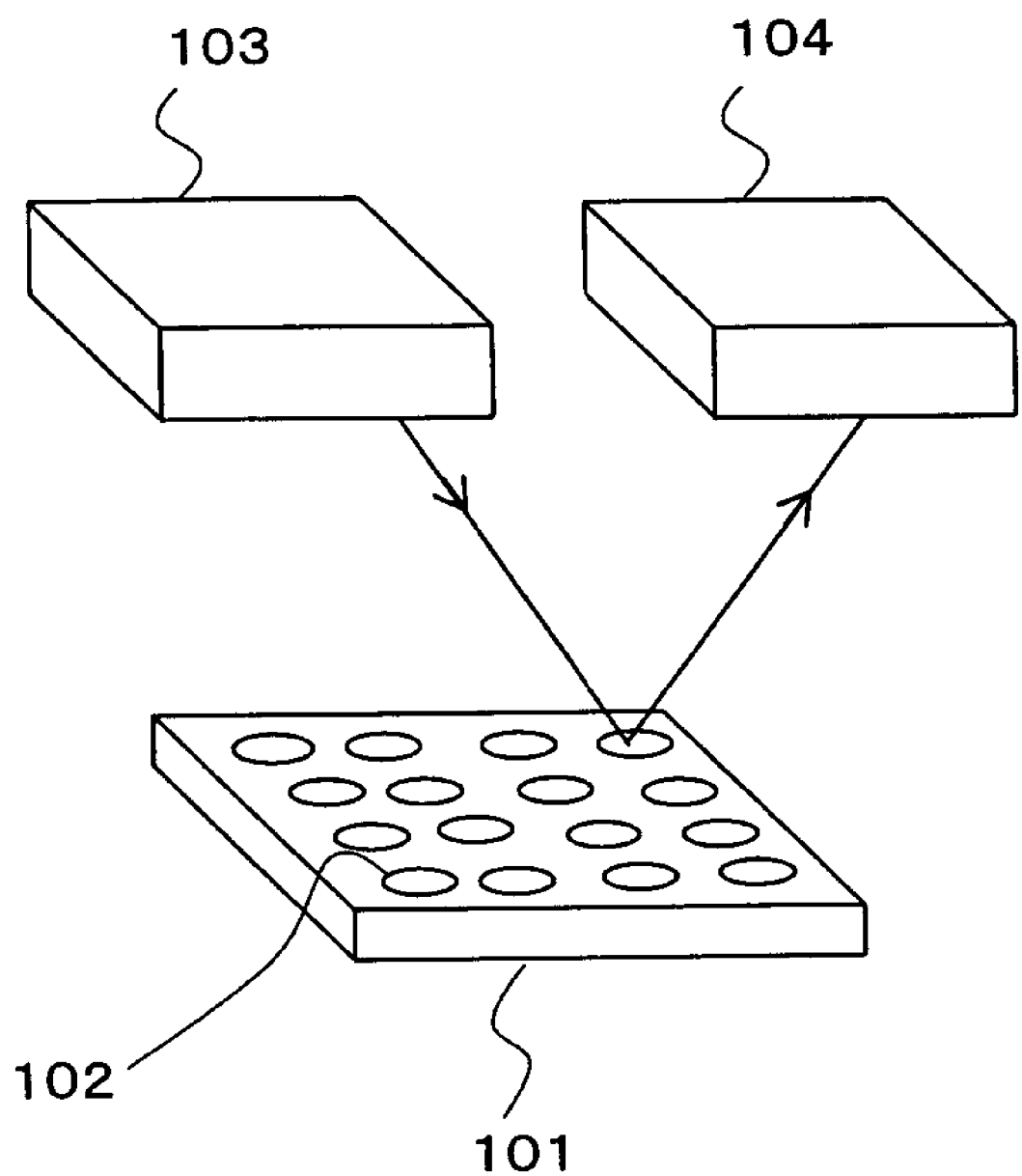
FIG. 16 is a schematic perspective view of a conventional analysis apparatus.

The construction of the light-shielding unit 39 is not restricted to that shown in FIG. 15(b). FIG. 15(c) shows another form of the light-shielding unit 39 of the selecting unit 27a shown in FIG. 15(a), where transparent electrodes, such as ITO's, are used as the electrodes 41. In this case, the electrodes 41 can be located between the liquid crystal portion 40 and the optical fibers 26, 30.

Such modified constructions that the other selecting units shown in FIGS. 12-15 are used in place of the foregoing selecting units 27a-27d, 31 can form the analysis apparatus C and achieve the advantages similar to those of foregoing description.

The selecting units 27a-27d, 31 may also have structures the same as those of the light path selecting unit 13 or 16 of the analysis apparatus A or B. In such cases, the light path selecting unit 13 or 16 should be able to establish an optical path formed by the light from the desired spot 2 to the photomultiplier tube 4 so as to transmit the light from the desired spot 2 to the photomultiplier tube 4 selectively.

Though the selecting units 27a-27d, 31 have the same constructions in the above described analysis apparatus C, they may have different constructions from those of each other.

The analysis apparatus C can detect any other types of lights such as emitted lights by other mechanisms like electrochemiluminescence or biochemiluminescence, as well as lights induced by excitation like fluorescence and phosphorescence, reflection lights, and transmitted lights. When an incident light is necessary for the analysis, a light source for the incident light may be provided, as illustrated in FIG. 4.

4. The Others

Although the first, second, and third embodiments of the present invention have been described, the present invention is not restricted to the embodiments. It is to be understood that modifications and variations like following examples are possible if necessary.

For example, the first, second, and third embodiments may be carried out in combination, such as the analysis apparatus C of the third embodiment may have a light source 14 described in the first embodiment in order for the lights like fluorescence or phosphorescence, which need to be excited by an excitation light, to be detected.

For another example, the condenser 5, 15, or 22 may be removable. Especially in case that the selectively light-transmitting unit is modularized into the condenser 5, 15, or 22, like above-mentioned embodiments, it is possible to enhance the replaceability thereof, to reduce the parts count owing to the simple constitution thereof. And in that case, the selecting section, which needs to be a delicate structure, can be surrounded by a somewhat strong construction. These characteristics lead to the advantage of the increase in longevity, the prevention of the malfunction, and the improvement in maintenance-bearing capacity.

For still another example, the analysis chip 1 may be formed with metal layers and gratings so as to detect surface plasmon resonance. Pay attention to that the light detected in the analysis using surface plasmon resonance is generally not a visible radiation. However, in this specification, the light to be detected is not restricted to a visible radiation, but any other types of lights with shorter or longer range of wavelength can be detected as mentioned earlier.

For further example, the spots 2 on the analysis chip 1 may be fabricated without the specific materials causing the interaction described earlier. That is, any kinds of spots 2 can be used as far as it can hold the samples to be detected, which may be changed in accordance with the object of the analysis, when the lights from the spots 2 are detected. Thus, there are no restrictions about samples in their sorts and amounts, in the present invention. That is, any kinds of samples can be analyzed as far as it can be a subject of the optical analysis.

To compare the conventional analysis apparatus and the one of the present invention, the conventional analysis apparatus, of the patent publication 1 as an example, selects the spot to be detected by changing the position of the analysis chip. This conventional analysis apparatus requires a driving mechanism for moving the analysis chip, and thus likely to be upsized. Furthermore, it takes relatively long to control for driving, which makes the apparatus to be difficult in conducting the analysis with high time resolution. While the analysis apparatus of the present invention requires no mechanism for conventional driving and thus can detect the lights from the desired spots 2 only by means of selecting the light paths.

The present invention can be used widely for the analysis of samples by means of detecting lights. It is particularly suitable for the analysis conducted utilizing an analysis chip, in areas such as chemistry or biology.

What is claimed is:

1. An analysis apparatus for analyzing samples by means of detecting lights from a plurality of spots formed on an analysis chip so as to hold the samples comprising:
   a chip holder for holding the analysis chip;
   a light detector for detecting lights from the plurality of spots; and
   a light-transmitting unit for transmitting lights selectively from a desired spot selected from the plurality of spots to the light detector, in a state where the analysis chip is held by the chip holder such that there is no relative motion of the analysis chip or the light detector.

2. An analysis apparatus as defined in claim 1, wherein said light-transmitting unit comprises:
   a light path forming section for forming a plurality of light paths, each starting from each of the spots to the light detector; and
   a light path selecting unit for successively selecting one from the plurality of light paths as the light path starting from the desired spot so that the desired spot is switched from one to another.

3. An analysis apparatus as defined in claim 2, wherein each of said plurality of light paths comprises an optical transmission medium provided for each of the plurality of spots and having a light-inputting end for receiving light from each of the spots and a light-outputting end for outputting light to the light detector.

4. An analysis apparatus as defined in claim 3, wherein said selectively light-transmitting unit comprises a light-outputting end holder for holding a plurality of the light-outputting ends of the optical transmission media on a circumference of a circle.

5. An analysis apparatus as defined in claim 3, wherein said light path selecting unit includes a light-outputting end moving unit for moving the light-outputting ends of the optical transmission media selectively into positions where optical paths from the desired spots to the light detector are established.

6. An analysis apparatus as defined in claim 3, wherein said light path selecting unit includes a selectively optical transmission medium having a selected-light inputting end for inputting the lights from the light outputting ends of the optical transmission media and a selected-light outputting end for outputting the light from the selected-light inputting end, and a selected-light inputting end moving unit for moving the selected-light inputting end selectively into a position where optical paths from the desired spots to the light detector are established.

7. An analysis apparatus as defined in claim 2, wherein said light path selecting unit includes a Garvano mirror arranged to be rotatable for selecting the light paths by reflection so as to establish optical paths from the desired spots to the light detector.

8. An analysis apparatus as defined in claim 2, wherein said light path selecting unit includes a polygon mirror having a plurality of specular surfaces and arranged to be rotatable for selecting the light paths by reflection so as to establish optical paths from the desired spots to the light detector.

9. An analysis apparatus as defined in claim 2, wherein said light path selecting unit includes a prism arranged to be movable for selecting the light paths so as to establish optical paths from the desired spots to the light detector.

10. An analysis apparatus as defined in claim 2, wherein said light path selecting unit includes a light shield arranged to be movable for selecting the light paths by blocking off lights from other spots so as to establish optical paths from the desired spots to the light detector.

11. An analysis apparatus as defined in claim 2, wherein said light path selecting unit includes a light path selecting electrical unit that has a liquid crystal and electrodes and that selects the light paths by applying a voltage to the liquid crystal using the electrodes so as to establish optical paths from the desired spots to the light detector.

12. An analysis apparatus as defined in claim 2, wherein each of said light paths includes a focusing lens for receiving and focusing the lights from each of the spots.

13. An analysis apparatus as defined in claim 2, wherein each of said light paths includes a stray lights rejector for rejecting lights from other than the corresponding spots.

14. An analysis apparatus as defined in claim 2, wherein said light path selecting unit further comprises a plurality of light path selecting units arranged hierarchically.

15. An analysis apparatus as defined in claim 1, wherein said light detector includes a photomultiplier tube.

16. An analysis apparatus as defined in claim 1, wherein each of said lights detected by the light detector is selected from the group consisting of chemiluminescence, electrochemiluminescence, biochemiluminescence, fluorescence, phosphorescence, reflection light and transmitted light.

17. A condenser used in an analysis apparatus, the analysis apparatus comprising a chip holder for holding an analysis chip having a plurality of spots for holding samples thereon and a light detector for detecting lights from the plurality of spots, wherein the condenser transmits lights selectively from the plurality of spots to the light detector without relative motion of the analysis chip or the light detector.

18. A condenser as defined in claim 17, the analysis apparatus further comprising a light path forming section for forming light paths, each light path starting from a respective one of the plurality of spots and ending at the light detector, and a light path selecting unit for transmitting lights selectively from the plurality of spots to the light detector by means of selecting the light paths.

19. A condenser as defined in claim 18, wherein each of said light paths includes an optical transmission medium corresponding to the respective one of the plurality of spots and having a light-inputting end for receiving the light from the respective one of the plurality of spots and a light-outputting end for outputting the light to the light detector.

20. A condenser as defined in claim 19, the analysis apparatus further comprising a light-outputting end holder for holding the light-outputting ends of the optical transmission media on a circumference of a circle.

21. A condenser as defined in claim 19, wherein said light path selecting unit includes a light-outputting end moving unit for moving the light-outputting ends of the optical transmission media selectively into positions where optical paths from the desired spots to the light detector are established.

22. A condenser as defined in claim 19, wherein said light path selecting unit includes a selectively optical transmission medium having a selected-light inputting end for inputting the lights from the light outputting ends of the optical transmission media and a selected-light outputting end for outputting the light from the selected-light inputting end, and a selected-light inputting end moving unit for moving the selected-light inputting end selectively into a position where optical paths from the desired spots to the light detector are established.

23. A condenser as defined in claim 18, wherein said light path selecting unit includes a Garvano mirror arranged to be rotatable for selecting the light paths by reflection so as to establish optical paths from the desired spots to the light detector.

24. A condenser as defined in claim 18, wherein said light path selecting unit includes a polygon mirror having a plurality of specular surfaces and arranged to be rotatable for selecting the light paths by reflection so as to establish optical paths from the desired spots to the light detector.

25. A condenser as defined in claim 18, wherein said light path selecting unit includes a prism arranged to be movable for selecting the light paths so as to establish optical paths from the desired spots to the light detector.

26. A condenser as defined in claim 18, wherein said light path selecting unit includes a light shield arranged to be movable for selecting the light paths by blocking off lights from other spots so as to establish optical paths from the desired spots to the light detector.

27. A condenser as defined in claim 18, wherein said light path selecting unit includes a light path selecting electrical unit that has a liquid crystal and electrodes and that selects the light paths by applying a voltage to the liquid crystal using the electrodes so as to establish optical paths from the desired spots to the light detector.

28. A condenser as defined in claim 18, wherein each of said light paths includes a focusing lens for receiving and focusing the lights from each of the plurality of spots.

29. A condenser as defined in claim 18, wherein each of said light paths includes a stray lights rejector for rejecting lights from other than the respective one of the plurality of spots.

30. A condenser as defined in claim 18, wherein said light path selecting unit further comprises a plurality of light path selecting units arranged hierarchically.

\* \* \* \* \*

UNITED STATES PATENT AND TRADEMARK OFFICE
CERTIFICATE OF CORRECTION

PATENT NO. : 7,632,463 B2
APPLICATION NO. : 11/274923
DATED : December 15, 2009
INVENTOR(S) : Hidehito Takayama et al.

It is certified that error appears in the above-identified patent and that said Letters Patent is hereby corrected as shown below:

On the title page item (73) should read:

Assignee: Mitsubishi Chemical Medience Corporation, Tokyo (JP)

Signed and Sealed this

Seventh Day of September, 2010

David J. Kappos
*Director of the United States Patent and Trademark Office*